United States Patent [19]
Ramage et al.

[11] Patent Number: 5,644,036
[45] Date of Patent: Jul. 1, 1997

[54] PURIFIED IMMUNOGLOBULIN

[75] Inventors: Paul Ian Nicholas Ramage, Reinach, Switzerland; Geoffrey Allen, Beckenham, England

[73] Assignee: Burroughs Wellcome Company, Research Triangle Park, N.C.

[21] Appl. No.: 319,598

[22] Filed: Oct. 7, 1994

Related U.S. Application Data

[63] Continuation of Ser. No. 304,440, Sep. 12, 1994, which is a continuation of Ser. No. 985,272, Dec. 3, 1992, abandoned, which is a continuation of Ser. No. 975,967, Nov. 13, 1992, abandoned, which is a continuation of Ser. No. 777,731, Oct. 16, 1991.

[30] Foreign Application Priority Data

Oct. 17, 1990 [GB] United Kingdom ............... 9022547-5

[51] Int. Cl.$^6$ ........................... C07K 1/18; C07K 1/22; C07K 1/36
[52] U.S. Cl. ................... 530/412; 435/69.6; 530/413; 530/416; 530/417
[58] Field of Search .................. 435/240.1, 240.27; 530/412, 413, 416, 417

[56] References Cited

FOREIGN PATENT DOCUMENTS

| | | |
|---|---|---|
| 0328404 | 2/1989 | European Pat. Off. . |
| 8905157 | 6/1989 | WIPO . |

OTHER PUBLICATIONS

Lambert et al. [J. Biol. Chem. 260(22):12035–12041 (1985)].
Lambert et al. [Cancer Treat Res 37:323–348 (1988)].
Harlow et al.[*Antibodies: A Laboratory Manual*, Cold Spring Harbor Press 285 (1988)].
Jiskoot, et al., *Develop. Biol. Standard*, 71 (1990), 73–78.
Bloom et al., *Journal of Immunological Methods*, 117 (1989), 83–89.
Carlsson et al., *Journal of Immunological Methods*, 79 (1985), 89–98.
Hartib Tech TIB Tech 11. 42–44 1993.
Lund Protocols in Molecular Biology J. Wiley & Sons 1987.
Waldmann Serve 252 1657–1661 1991.
Reichmann, L., et al., "Reshaping human antibodies for therapy," *Nature*, 332, 323–327 (Mar. 24, 1988).
Duffy, S. A., et al., "Recovery of Therapeutic–Grade Antibodies: Protein A and Ion–Exchange Chromatography," *BioPharm*, 2:6, 34–45 (Jun. 1989).
Kennedy, J.F., et al., "The use of HPLC in biotechnology," *Journal of Biotechnology*, 9:2, 83–106 (Jan. 1989).
Hale, G., et al., *Lancet*, 1394–1399 (1988).
Underwood, P.A., et al., *Meths. in Eng.* 121, 301–306 (1986).
Underwood, P.A., et al., "Use of Protein A to Remove Immunoglobulins from Serum . . . " *J. Immunological Methods*, 60, 33–45 (1983).
Hale, G., et al., *Tissue Antigen*, 35, 118–127 (1990).

*Primary Examiner*—Donald E. Adams
*Attorney, Agent, or Firm*—Nixon & Vanderhye P.C.

[57] ABSTRACT

A purified preparation of an anti-CDW52 antibody which exhibits on size exclusion chromatography: a single peak under non-reducing conditions and two major peaks under reducing conditions.

The preparation preferably also exhibits on conventional SDS PAGE: one main band using a non-reduced sample and two main bands using a reduced sample.

Additionally the preparation exhibits on reversed phase HPLC: a single sharp peak under non-reducing conditions and two major peaks under reducing conditions. Also a process of purifying an anti-CDW52 antibody, formulations containing such a purified preparation and uses thereof.

6 Claims, 6 Drawing Sheets

GDEV-95

MWM-molecular weight markers
NR-non-reduced
N-reduced

Fig. 3

Reverse-phase / Non-reduced

Fig. 4

Reverse-phase / Reduced

Analysis 6.1W
SAMPLE B005   1059 200690    10:59 20/6/90
Method: RP (RCM) CP1H

| RETN TIME | PEAK HT | PEAK AREA | %AREA | PEAK NO. | PEAK START | PEAK END |
|---|---|---|---|---|---|---|
| 23.52 | .15 | 7.00 | .590 | 1 | 22.08B | 24.20B |
| 26.90 | 3.96 | 229.71 | 19.370 | 2 | 25.10B | 29.88B |
| 36.83 | 13.81 | 643.29 | 54.245 | 3 | 35.43B | 39.27V |
| 39.62 | .15 | 8.27 | .697 | 4 | 39.27V | 41.18B |
| 51.17 | .59 | 51.71 | 4.360 | 5 | 50.35B | 53.40B |
| 67.65 | 1.01 | 171.79 | 14.486 | 6 | 63.65V | 67.75V |
| 68.03 | .91 | 74.13 | 6.251 | 7 | 67.75V | 69.98B |
|  |  | 1185.90 |  |  |  |  |

Plotting factors   64629.937   230.991

Fig. 5

Size Exclusion / Non-reduced

Fig. 6

Size Exclusion / Reduced

Analysis 6.1W
SAMPLE C104      1318 190690      13:18 19/6/90
Method : SEC RCM CP1H

| RETN TIME | PEAK HT | PEAK AREA | %AREA | PEAK NO. | PEAK START | PEAK END |
|---|---|---|---|---|---|---|
| .17 | .79 | 11.14 | .139 | 1 | .08B | 1.38B |
| 5.90 | .01 | .07 | .001 | 2 | 5.75B | 6.00B |
| 7.48 | 1.08 | 15.26 | .191 | 3 | 7.13B | 7.55V |
| 7.80 | 1.39 | 59.61 | .745 | 4 | 7.55V | 8.43V |
| 9.05 | 57.07 | 1838.27 | 22.965 | 5 | 8.43V | 10.23V |
| 10.72 | 23.52 | 876.32 | 10.948 | 6 | 10.23V | 12.33B |
| 14.17 | .00 | .09 | .001 | 7 | 13.88B | 14.32B |
| 15.88 | 1.37 | 15.60 | .195 | 8 | 15.80B | 16.05B |
| 16.52 | 19.18 | 310.43 | 3.878 | 9 | 16.10B | 16.63V |
| 17.20 | 94.47 | 4877.93 | 60.938 | 10 | 16.63V | 20.60B |
|   |   | 8004.72 |   |   |   |   |

Plotting factors    10058.756    -94.960

PURIFIED IMMUNOGLOBULIN

This is a continuation of application Ser. No. 08/304,440, filed Sep. 12, 1994, which is a continuation of application Ser. No. 07/985,272, filed Dec. 3, 1992, abandoned which is a continuation of Ser. No. 07/975,967, filed Nov. 13, 1992, abandoned which is a continuation of Ser. No. 07/777,731, filed Oct. 16, 1991.

The present invention relates to a purified preparation of monoclonal antibodies against the antigen $CD_w52$, to their use in therapy and to processes for their production.

Antibodies or immunoglobulins are proteinaceous bi-functional molecules. One region which is highly variable between the different antibodies, is responsible for binding to an antigen, for example many different infectious agents that the body may encounter, whilst the second, constant region is responsible for binding to the Fc receptors of cells and also activates complement. In this way antibodies represent a vital component of the immune response of mammals in destroying foreign microorganisms and viruses. Immunisation of an animal with an antigen results in the production of polyclonal antibodies, in other words, different antibodies with different specificities and affinities. For therapeutic applications it is advantageous to be able to produce antibodies from a single lymphocyte clone—such antibodies are called monoclonal antibodies and are specific to a particular determinant of the original antigen. They can be obtained by the method of Kohler and Milstein (Nature, 1975, 256, 495–497).

A single antibody molecule of the IgG class is composed of two light chains and two heavy chains that are held together by interchain disulphide bonds. Each light chain is linked to a heavy chain by a disulphide bond and the two heavy chains are linked to each other by disulphide bonds. Each heavy chain has at one end a variable domain followed by a number of constant domains, each light chain has a variable domain at one end and a constant domain at the other end. The light chain variable domain is aligned with the variable domain of the heavy chain. The light chain constant domain is aligned with the first constant domain of the heavy chain. The remaining constant domains of the heavy chains are aligned with each other and form the Fc fragment, after limited cleavage of the polypeptide chain.

The variable domains of each pair of light and heavy chains form the antigen binding site. Together with the first constant domain of the heavy chain and the constant domain of the light chain they form, after limited cleavage of the polypeptide chain, the Fab fragment. The variable domains of each pair of heavy and light chains have the same general structure with each domain comprising a framework of four regions, whose sequences are relatively conserved, connected by three complementarity determining regions (CDRs). The four framework regions largely adopt a β-sheet conformation and the CDRs form loops connecting, and in some cases comprising part of, the β-sheet structure. The CDRs are held in close proximity by the framework regions and, with the CDRs from the other domain, contribute to the formation of the antigen binding site.

The antigen $CD_w52$ (G. Hale et al, Tissue Antigens 1990 35, pp 118–127) is an abundant molecule widely distributed on most, if not all, human lymphocytes. It is also present on the surface of the majority of malignant lymphocytes, but not haemopoietic cells, nor is it expressed on granulocytes, platelets, erythroid or myeloid bone marrow cells. A number of monoclonal antibodies of different isotypes have been raised against this antigen and reported in the literature, (G. Hale et al Tissue Antigens, 1990, 35, pp 118–127). One of these antibodies, an IgG1 antibody, has been humanised (Nature, 1988, 322, 323–327 and EPO328404). This antibody is known as Campath 1H (Campath is a trademark of The Wellcome Foundation Ltd). A preparation of this antibody has been used to treat patients suffering from Non Hodgkins' lymphoma, (G. Hale et al, Lancet, 1988, pp 1394–1399).

Campath 1H was originally purified in a one-step process on a Protein A Sepharose column (EPO328404). Protein A is a group specific ligand which binds to the Fc region of immunoglobulin; therefore other immunoglobulins contained in serum present in the culture medium will co-purify with the immunoglobulin of interest thereby contaminating the end product (P. A. Underwood et al, Meths. in Enzymol. 121 pp. 301–306 (1986), and P. A. Underwood et al, J.Immunol. Meths 60, 33, 1983). Antibodies which are intended for use in medical therapy may need to be administered repeatedly, so the need to remove foreign immunoglobulins is important as such administration may produce an immune response and induce nephrotoxicity, serum sickness and in severe cases anaphylactic shock. Whole animal serum or serum albumin will contain other proteins, lipids and carbohydrates; these molecules may themselves raise an immune response but pose a greater danger of harbouring pathogens such as the agent which causes Bovine Spongiform Encephalopathy (BSE). Endotoxins may also be present which are undesirable as they produce potentially fatal pyrogenic responses.

Other contaminants in the culture medium containing the expressed antibody, include host cell and viral nucleic acid. Also aggregates of antibodies as they too may act as immunogens and cause an undesirable immune response.

The present invention therefore provides a purified preparation of an anti-CDw52 antibody which exhibits on size exclusion chromatography:

a single peak under non-reducing conditions and two major peaks under denaturing and reducing conditions.

The preparation preferably also exhibits on conventional SDS polyacrylamide gel electrophoresis:

one main band using a non-reduced sample and two main bands using a reduced sample.

Additionally the preparation exhibits on reversed phase HPLC:

a single sharp peak under non-reducing conditions and two major peaks under reducing conditions.

Size exclusion chromatography as its name suggests separates on the basis of the size of proteins. In general separation occurs when large molecules are excluded from entering the porous stationary phase and are carried straight through the column while progressively smaller molecules are increasingly able to enter the stationary phase and consequently have particularly longer elution times. It is the porosity of the stationary phase which therefore determines the separation achieved. This analytical technique is particularly good for determining levels of aggregate in the purified preparation. The stationary phase is a wide pore silica gel which may be modified with diol groups preferably a gel such as Zorbax GF450-GF250 (Trademark of Dupont) or TSK gel G3000 SWXL or G4000 SWXL. The mobile phase is generally in the pH range 4–8 more preferably 6–7.5 advantageously around pH6.8. This phase is advantageously a mixture of a phosphate such as disodium hydrogen orthophosphate and a sulphate such as sodium or potassium sulphate and water. The molarity of such a mixture is generally 25 mM to 1M most preferably around 50 mM.

SDS polyacrylamide gel electrophoresis (SDS PAGE) gives information about the number and type of proteins present in a mixture, their relative abundance and a measure of their molecular weights. SDS is an anionic detergent, it is reacted with the proteins before electrophoresis. Most protein SDS complexes are soluble and will migrate through a polyacrylamide gel towards the anode, under the influence of an electrical charge. Rate of migration is generally inversely related to the logarithm of the molecular weight of the protein. It is convenient to carry out the SDS analysis on a gradient gel which may be flat bed or vertical slabs or rods. The gradient is advantageously 10–22% or more preferably 8–18%. The gel is preferably Pharmacia Excel (Trademark) gel.

Reversed phase HPLC separates on the basis of hydrophobicity. As with other HPLC techniques there is a polymeric stationary phase, of for example polystyrene/divinylbenzene. The mobile phase is usually a combination of a weak aqueous buffer or a dilute acid and a water miscible organic solvent. For effective separation of proteins the mobile phase is generally a gradient system, required to achieve separation and is preferably linear for convenience.

The stationary phase for analysis of immunoglobulin may be an organic polymeric matrix such as Polymer Labs PLRP-S generally of particle size around 8 µM; the pore size is preferably 300° A or 1000° A. The mobile phase is advantageously a mixture of an acid such as formic, acetic or trifluoroacetic acid, water and acetonitrile. The acid and the water are preferably present in the ratio 5:3.

An antibody can be reduced to its component heavy and light chains by reduction of the disulphide bonds under denaturing conditions with for example Guanidinium chloride and dithiothreitol. Subsequent alkylation of the free thiol groups, for example with iodoacetamide iodoacetic acid, assists in preventing the bonds from reforming.

A measure of purity is provided by the specific activity of the antibody preparation. Specific activity may be determined by the method set out in the Examples. A preparation according to the invention preferably has a specific activity of greater than 0.8 Kilo Units/mg, ideally greater than 0.9 Kilo Units/mg, most preferably around 1.0 Kilo Units/mg.

A purified preparation of an anti-CDW52 antibody according to the invention ideally, is substantially free from host cell contaminants such as host cell proteins, nucleic acids and endotoxins. Specific activity provides information about the levels of host cell protein in the preparation. Endotoxin levels may be measured by the LAL (Limulus Amoebocyte Lysate) method described in Parenteral Quality Control, M. J. Alles et al.; Marcel Dekker Inc., New York.

A preparation according to the invention is also essentially free from aggregate, as measured on size exclusion chromatography. It is desirable for these levels to be less than 2%, ideally less than 0.5%.

Antibodies according to the invention may be prepared using a recombinant expression system, the preferred system is a mammalian expression system using Chinese hamster ovary (CHO) cells. These may be dihydrofolate reductase (dhfr) deficient and so dependent on thymidine and hypoxanthine for growth (PNAS 77 1980, 4216–4220). The parental dhfr⁻CHO cell line is transfected with the antibody gene and dhfr gene which enables selection of CHO cell transformants of dhfr positive phenotype. Selection is carried out by culturing the colonies on media devoid of thymidine and hypoxanthine, the absence of which prevents untransformed cells from growing and transformed cells from resalvaging the folate pathway and thereby bypassing the selection system. These transformants usually express low levels of the product gene by virtue of co-integration of both transfected genes. The expression levels of the antibody gene may be increased by amplification using methotrexate (MTX). This drug is a direct inhibitor of the dhfr enzyme and allows isolation of resistant colonies which amplify their dhfr gene copy number sufficiently to survive under these conditions. Since the dhfr and antibody genes are more closely linked in the original transformants, there is usually concommitant amplification, and therefore increased expression of the desired antibody gene.

Another expression system for use with CHO or myeloma cells is the glutamine synthetase (GS) amplification system described in WO87/04462. This system involves the transfection of a cell with a gene encoding the GS enzyme and the desired antibody gene. Cells are then selected which grow in glutamine free medium. These selected clones are then subjected to inhibition of the GS enzyme using methionine sulphoximine (Msx). The cells, in order survive, will amplify the GS gene with concomitant amplification of the gene encoding the antibody.

Antibody is preferably obtained in a form in which it is secreted in to the culture medium. The harvested medium may then be filtered and/or concentrated by an ultrafiltration step to obtain an aqueous solution which is subjected to a purification procedure involving applying an aqueous solution of the antibody to a) a Protein A column so as to absorb the antibody onto the column, and then eluting the antibody with an acidic solution;

b) applying the acidic eluate to an ion-exchange column of charged particles so as to absorb the antibody, and then eluting the antibody with an aqueous solution of counter-charged ions;

c) applying the aqueous eluate to a size exclusion column of porous particles so as to separate according to molecular size and to obtain the desired antibody in selected fractions eluted from the column.

Protein A is a group specific ligand which binds to the Fc region of most IgG. It is synthesised by some strains of staphylococcus aureus and can be isolated from culture supernatants then insolubilised by coupling to agarose beads or silica. An alternative method is to use whole bacteria of a strain which carries large amounts of protein A on the bacterial cell surface. Both types of gel preparation are available commercially. (Protein A—Pharmacia. Whole bacteria Calbiochem, IgG sorb). (Alan Johnstone and Robin Thorpe Immunochemistry in practice, Blackwell Scientific Publn. Chpt.10). An alternative to Protein A is Protein G (Analytical Chem. Vol. 61 (13) 1989 1317).

The column which is most preferably used is a Protein A Sepharose column particularly Protein A Sepharose Fast Flow (Trademark). Ideally the column is washed with trio or phosphate buffered saline around pH7.0 and the antibody is eluted at acid pH 3.0–3.5 advantageously pH 3.0 using an acid such as citric acid for example in a concentration of about 1.0M.

Ion-exchange chromatography exploits interactions between charged groups in a stationary phase and the sample which is in a mobile phase. The stationary phase of an ion-exchange column may be a positively charged cation exchanger or a negatively charged anion exchanger. The charged groups are neutralised by oppositely charged counter ions in the mobile phase, the counter ions being replaced during chromatography by more highly charged sample molecules. It is preferable to use cross-linked columns based for example on agarose for example S-Sepharose Fast Flow (Trademark) cation exchange column particularly S.Sepharose Fast Flow cation exchange (Trademark). Alternatively a membrane-based column could be employed. The column is usually washed after application of the eluate from the Protein A column, with 20 mM HEPES buffer pH 7.5 and the antibody is eluted with the same buffer containing sodium chloride in the range 0.2M to 0.075M.

Size exclusion chromatography as its name suggests separates on the basis of the size of proteins. In general separation occurs when large molecules are excluded from entering the porous stationary phase and are carried straight through the column while progressively smaller molecules are increasingly able to enter the stationary phase and consequently have particularly longer elution times. It is the porosity of the stationary phase which therefore determines the separation achieved. Suitable materials are chemically bonded and provide resistance to compression for example an agarose and/or dextran composition such as Superdex (Trademark). A preferred column is a Superdex 200 size exclusion medium. The eluate from the ion exchange column is preferably applied to the Superdex column and developed in buffer in the range pH5–8 preferably PBS pH 7.2.

Each column is preferably protected by a filter which may be a 0.2μ Gelman Acro sterilising filter or in the case of the Protein A column a PALL posidyne SLK 7002 NFZP or a PALL DSLK2 filter (available from Pall Process Filtration Ltd. European House, Havant Street, Portsmouth 301 3PD) and for the other two columns a Millipak filter preferably Millipak 100 for the ion exchange column and Millipak 20 or 60 for the size exclusion column (available from Millipore, The Boulevard, Blackmore Lane, Warford, Herts. The columns are preferably sanitised before use with an appropriate sanitant for example 0.5M NaOH for 16 hours for any of the columns, or 2% hibitane gluconate in 20% ethanol for the Protein A column or 1N NaOH for the other two columns. Sanitants were washed out with the appropriate sterile buffers before applying the protein solution. All solutions used in the process were preferably sterile and endotoxin free.

Additional steps may be added to the purification procedure set out above. Ultrafiltration may be used to further reduce viral and host cell nucleic acid contamination. This may be carried out using commercially available ultrafiltration units such as Viresolve/70' or Viresolve/180' membranes additionally, PLMK regenerated cellulose 300 k cut off membrane all available from Millipore, The Boulevard, Blackmore Lane, Watford, Herts. An alternative method to reduce virus contamination is microfiltration using a Nylon membrane in cartridge form for example Nylon 66,0.04M membrane from PALL.

A purification step to remove contaminating DNA may be introduced, for example, a wash of the Protein A column using NaCl in the range 1M–3M in buffer at neutral pH preferably PBS at pH7.2. Glycine may be added to the NaCl preferably at about 1.5M in the pH range 8.8–9.0.

An anti-$CD_w52$ antibody of the present invention may be a monoclonal antibody obtained from a hybridoma of murine or rat origin and/or may be obtained using recombinant DNA technology.

Recombinant DNA technology has provided the ability to develop altered antibodies of two basic types. The first type, referred to as chimeric antibodies, is where the rodent constant domains only are replaced by equivalent domains of human origin (Morrison et al, *P.N.A.S.*, 1984, 81, 6851–6855; Boulianne et al, *Nature*, 1985, 314, 268–270; and Neuberger et al, *Nature*, 1985, 314, 268–270). The second type is where the murine constant domains and the murine framework regions are all replaced by equivalent domains and regions of human origin. This second type of antibody is referred to as a humanised or CDR-grafted antibody (Jones et al, *Nature*, 1986, 321, 522–525; and Riechmann et al, *Nature*, 1988, 332, 323–327). These antibodies more closely resemble human antibodies when administered to a human patient and so do not elicit an anti-antibody response to the same degree. A human antibody could also be used.

Accordingly the purified anti-$CD_w52$ antibody of the invention may be a rat, mouse or human antibody wherein the amino acid sequences of the heavy and light chains are homologous with those sequences of antibody produced by the species lymphocytes in vivo or in vitro by hybridomas. Preferably the anti-CDw52 antibody is an altered antibody such as a hybrid antibody in which the heavy and light chains are homologous to a natural antibody but are combined in a way that would not occur naturally. The antibody may be chimaeric antibody which has variable regions from one antibody and constant regions from another. Thus, chimaeric antibodies may be species/species chimaeras or class/class chimaeras. Such chimaeric antibodies may have one or more further modifications to improve antigen binding ability or to alter effector functioning. Another form of altered antibody is a humanised or CDR-grafted antibody including a composite antibody, wherein parts of the hypervariable regions in addition to the CDRs are transferred to the human framework. Additional amino acids in the framework or constant regions of such antibodies may be altered. Thus within the scope of the invention is included, any anti-CDw52 altered antibody in which the amino acid sequence is not one which exists in nature. However, CDR-grafted antibodies are most preferred of which Campath 1H (Trademark of The Wellcome Foundation Ltd.) is an example. The antibody chain DNA sequences including the CDRs of Campath 1H are set out in EP0328404, the disclosure of which is hereby incorporated by reference. The invention therefore includes a purified preparation of an anti-CDw52 antibody wherein the antibody comprises one or more of the CDR sequences set out in EP0328404.

Purified anti-CDw52 antibodies are useful in medical therapy for treating numerous human disorders, generally as immunosuppresstves more particularly for example T-cell mediated disorders including severe vasculitis, rheumatoid arthritis, systemic lupis, also autoimmune disorders such as multiple sclerosis, graft vs host disease, psoriarsis, juvenile onset diabetes, Sjogrens' disease, thyroid disease, myasthenia gravis, transplant rejection and asthma. These antibodies are also useful in treating cancers such as Non-Hodgkins lymphoma and leukemias.

The invention therefore provides the use of a purified preparation of an anti-CDw52 antibody in the manufacture of a medicament for the treatment of any of the aforementioned disorders. Also provided is a method of treating a human being having any such disorder comprising administering to said individual a therapeutically effective amount of a purified preparation of an anti-CDw52 antibody.

The dosages of such antibodies will vary with the condition being treated and the recipient of the treatment, but will be in the range 1 to about 100 mg for an adult patient, preferably 1–10 mg, usually administered daily for a period between 1 and 30 days. A two part dosing regime may be preferable wherein 1–5 mg are administered for 5–10 days followed by 6–15mg for a further 5–10 days.

Also included within the invention are formulations containing a purified preparation of an anti CDw52 antibody. Such formulations preferably include, in addition to antibody, a physiologically acceptable diluent or carrier possibly in admixture with other agents such as other antibodies an antibiotic. Suitable carriers include but are not limited to physiological saline, phosphate buffered saline, phosphate buffered saline glucose and buffered saline. Alternatively, the antibody may be lyophilised (freeze-dried) and reconstituted for use when needed, by the addition of an aqueous buffered solution as described above. Routes of administration are routinely parenteral including intravenous, intramuscular, subcutaneous and intraperitoneal injection or delivery.

The accompanying drawings show:

FIG. 1

(a) the pLD9 construct containing expression cassettes for the 'crippled' dhfr selection/amplification marker and the Campath-1H light chain cDNA. The small box with the dashed arrow is the weakened SV40 promoter; the larger dotted box with an arrow is the β-actin promoter; polyA refers to respectively sourced polyadenylation and termination signals; the small box with ori contains the SV40 origin of replication;

(b) the pNH316 construct containing expression cassettes for the neomycin selection marker and the Campath-1H heavy chain cDNA. The box with an arrow and MT refers to the mouse metallothionein promoter. Restriction sites indicated are: H, HindIII; Bg, BglII; B, BamHI; R1, EcoR1.

FIG. 2

SDS polyacrylamide gel of non-reduced and reduced Campath 1H showing a single main band.

FIG. 3

Reversed phase high performance chromatograph of non-reduced Campath 1H showing a single peak.

FIG. 4

Reversed phase high performance chromatograph of reduced and carboxymethylated Campath 1H showing two resolved peaks corresponding to the heavy and light chains of the antibody.

FIG. 5

High performance size exclusion chromatograph of non-reduced Campath 1H showing a single peak.

FIG. 6

High performance size exclusion chromatograph of reduced Campath 1H showing two major peaks.

EXAMPLE 1

Production of Campath 1H from CHO cells

EXAMPLE 1A

Cloning of the Heavy and Light Chain cDNAs for Campath-1H

The complementarity determining regions from the rat Campath-1G monoclonal were originally grafted directly into genomic human heavy and light chain frameworks (Winter et al, *Nature*, 1988, 322, 323–327). These constructs were engineered for expression in the myeloma cell line YO and resulted in yields of Campath-1H of up to 5 µg/ml following 10–14 days in culture (Hale et al, *Tissue Antigens*, 1990, 35, 118–127 and Winter et al, *Nature*, 1988, 322, 323–327). The myeloma cell line TF57 (Hale et al, *ibid.*) was used to generate size selected cDNA fractions of 0.9–1.2kb and 1.4–1.7 kb for the light and heavy chain cDNAs respectively. These were used to make EcoR1 linkered cDNA libraries in λgt10. All procedures were as described by Huynh et al (*DNA Cloning*, Vol I: A Practical Approach, 1984, Glover, D. (Editor), IRL Press, Oxford). The libraries were screened using [$^{32}$P] nick translated probes specific for the variable regions to isolate full length cDNA clones. For the light chain cDNA, the 5' untranslated leader was removed up to position −32 using Bal-31 exonuclease and a HindIII linker added. For the 3' end, use was made of a unique SacI site 47 bp upstream of the stop codon. A SacI-HindIII synthetic oligonucleotide pair was used to regenerate this sequence and position the HindIII site immediately after the stop codon. For the 5' end of the heavy chain cDNA, the unique NcoI site overlapping the ATG start codon was used to re-build a 29 bp untranslated leader, identical to that of the light chain, using a HindIII-NcoI oligonucleotide pair. At the 3' end, the unique NaeI site 12 bp downstream of the stop codon was converted into a HindIII site using linkers.

EXAMPLE 1B

Construction of Vectors:

The human β-actin promoter was excised from pHβAPr-3-neo (which corresponds to pHβAPr-1-neo (Gunning et al, *P.N.A.S.*, 1987, 84, 483–35) except that the SV40 polyadenylation/termination signal has been replaced with the respective human β-actin signals) as a 2860 bp PvuII-HindIII fragment, in which the PvuII site was subsequently converted to a BglII site using linkers. To isolate the human β-actin polyadenylation and termination signals from pHβAPr-3-neo, an SphI site 1.4 kb downstream of the unique HindIII site was converted to a BamHI site using linkers. The basal dhfr vector called p104, was constructed as follows. The SphI site at position −128 in the SV40 promoter in pSV2dhfr (Subramani et al, *Mol.Cell.Biol.*, 1981, 1, 854–864) was converted into a SalI site to remove all enhancer elements from the promoter. The weakened dhfr expression unit was then subcloned as a SalI-BamHI fragment into the homologous sites in pSVOd (Mellon et al, *Cell*, 1981, 27, 279–288).

Figure 1A:
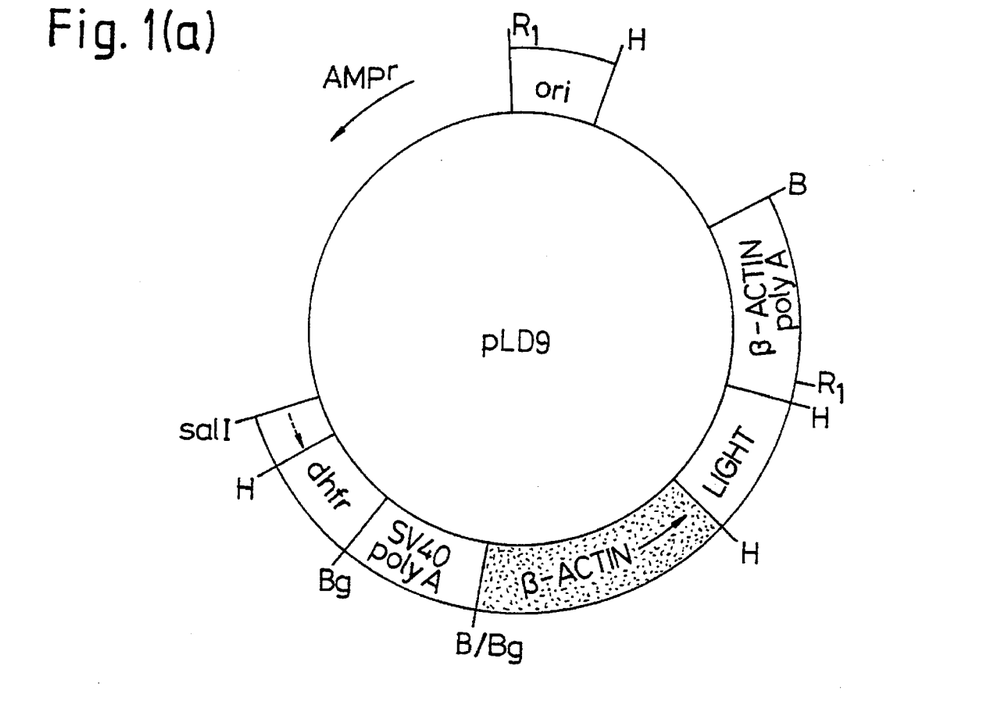
Figure 1B:
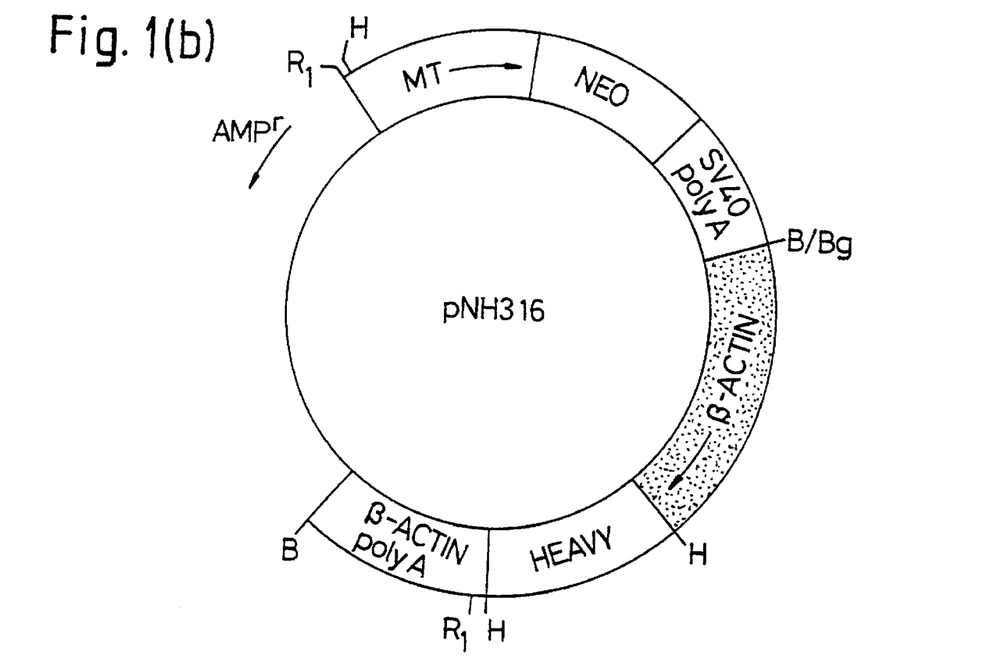

To construct pLD9, the p104 vector was digested with BamHI, phosphatased, and ligated with three other fragments consisting of the BglII-HindIII β-actin promoter, the HindIII Campath-1H light chain cDNA and the HindIII-BamHI β-actin polyA/termination signals. To construct pNH316, the construct pdBPV-MMTneo (Law et al, *Mol.Cell.Biol.*, 1983, 3, 2110–2115) was digested with BamHI, phosphatased, and the fragment containing the neomycin gene isolated following separation on an agarose gel. This was ligated to the two β-actin fragments and the Campath-1H heavy chain cDNA. The constructs, pLD9 and pNH316 are depicted in FIG. 1.

EXAMPLE 1C

Expression of Campath-1H in CHO Cells:

The dhfr⁻ CHO cell line DUK-Bll (Urlaub et al, *P.N.A.S.*, 1980, 77, 4216–4220) was grown in Iscove's MEM supplemented with 10% fetal bovine serum, and 4 µg/ml each of hypoxanthine and thymidine. 10 µg of pLD9 and pNH316 was co-precipitated onto cells using the calcium phosphate method, (Gorman et al, *DNA Cloning*, 1985, Vol II, 143–190, Academic Press, N.Y.) and selected for the double phenotype of dhfr⁺/neo resistance by using the medium above except that 10% dialysed serum was used, the hypoxanthine/thymidine were omitted, and G418 (Gibco) was included at 500 µg/ml. In some experiments MTX was included directly in the first round selection for dhfr⁺ transformants. Several hundred resistant colonies were pooled and assayed for the production of Campath-1H antibody in the culture medium. The average yield was 0.5 µg/ml for non-amplified first round transformants.

Each pooled cell population was then cultured in the presence of $10^{-7}$M MTX, and after two weeks, resistant colonies were again pooled and titred for Campath-1H production. There was a considerable increase in yield of up to 80-fold (Table 1). These cells were dilution cloned, screened for Campath-1H yield, and two high producer lines isolated, called A37 and 3D9 (Table 1). These were both amplified further in the presence of $10^{-6}$M MTX, then dilution cloned and screened as above. The increase in expression at this second, and final, amplification stage was not so dramatic as seen previously; nevertheless, when re-fed at confluence and left for a further 4 days, the cell lines A39 and 3D11 were capable of producing up to 200 μg/ml of Campath-1H.

TABLE 1

Expression Levels of Campath-1 H using Stepwise Amplification

| Construct | Selection stage | Accumulated Campath-1 H (μg/ml) |
|---|---|---|
| pLD9 + pNH316 | dhfr⁺/neo basal pool | 0.5 |
| | $10^{-7}$ M MTX amplified pool | 18–40 |
| | Cell lines A37 and 3D9 | 40 |
| | $10^{-6}$ M MTX amplified pool | 60–90 |
| | Cell line A39 | 100 |
| | Cell line 3D11 | 150–200 |

Cells were allowed to reach confluence in a T-175 tissue culture flask, then re-fed with fresh 50 ml of tissue culture medium and left for a further 4 days. The Campath-1H antibody that had accumulated in the medium during this period was measured by ELISA. Total cell counts on the day of assay were usually $2.5\times10^7$. The yield from the 3D11 cell line reflects a productivity of 100 μg/$10^6$ cells/day.

The co-transfection vectors pLD9 and pNH316 were further employed to evaluate an alternative amplification strategy to the one described above. The dhfr⁻ CHO cells were co-transfected as usual, and two days later split directly into a series of flasks containing G418 (for neomycin selection) and increasing concentrations of MTX ranging from $3\times10^{-9}$M to $10^{-7}$M. Following two weeks of this selection, the number of resistant colonies were counted and pooled for each flask. When the cell populations had stabilized, they were assayed for Campath-1H antibody titres and the results are shown in Table 2. As the MTX level was increased, there was a marked decrease in the number of surviving dhfr⁺ colonies, but they express proportionately more Campath-1H. Thus, in a one step direct selection at high concentrations of MTX, it is possible to isolate cell populations which produce up to 60-fold increase in antibody yield compared to cell populations selected for basal dhfr levels.

TABLE 2

Expression Levels of Campath-1 H using Direct Selection

| Selection (M MTX) | dhfr⁺ colonies | Accumulated Campath-1 H (μg/ml) |
|---|---|---|
| No MTX | 500 | 0.5 |
| $3\times10^{-9}$ | 40 | 2 |
| $10^{-8}$ | 5 | 7 |
| $3\times10^{-8}$ | 5 | 30 |
| $10^{-7}$ | — | — |

Colonies at each MTX selection stage were pooled and assayed as described in the legend of Table 1.

This selection procedure was repeated following another co-transfection of cells, and in this instance, the entire population was selected in medium containing G418 and $3\times10^{-8}$M MTX. This generated a larger pool of resistant colonies which were subsequently pooled and re-amplified twice more using MTX concentrations of $6\times10^{-7}$M, then $3\times10^{-6}$M. At this stage, the cells were dilution cloned and screened for Campath-1H levels. The two highest producer cell lines isolated were capable of producing antibody levels up to 100–150 μg/ml and were designated as lines 4F11 and 5E10.

The growth rates of these cell lines, and the A39/3D11 lines described above, were considerably slower than the parental non-transformed dhfr⁻ CHO cells. This is usually a common feature of these cells once they have been engineered to express high quantities of a product gene. The yields from the 5E10 and 4F11 cell lines proved to be quite variable over time, and the latter appeared to have only a limited passage life lasting about 3 weeks before entering crisis and death. This instability was not evident at all in the other cell lines, although in general, the lines isolated from the second amplification procedure, including 5E10, were usually more fickle to culture. Of all the lines, the 3D11 coupled good growth and stability with high Campath-1H yields. To ensure the propagation of these features, the 3D11 cell line was dilution cloned once more to generate the 3D11* line and this similarly produced Campath-1H yields up to 200 μg/ml.

EXAMPLE 2

Growth of and Production from C1H 3D11* 44 in Serum Free medium

C1H 3D11* cells growing as a monolayer in Iscoves +10% FBS Flow non-essential amino acids, $10^{-6}$M Methotrexate and antibiotics were approximately 90% confluent. These cells were removed from the plastic with trypsin/versene, washed in Iscoves medium without supplements centrifuged and resuspended at $5\times10^4$/ml in WCM4 medium set out in Table below +0.25% peptone +0.1% polyethylene glycol (PEG) 10,000+0.5% fetal bovine serum (FBS) without methotrexate (MTX). Three 25 cm² flasks were set up with 10 ml of cell suspension+hypoxanthine (H), thymidine (T) or HT. These flasks were incubated at 36.5° C. in 5% CO₂ incubator.

After six days, the contents of the flasks were pooled and added to an equal volume of medium+MTX without peptone or PEG, and were transferred to a 75 cm² flask.

These cells were used to seed a 500 ml Techne spinner, incubated at 36.5° C. spinning at 40 rpm. Cells continued growing serum free for a period of over five months and although it was found that the cells needed a period of adaptation, the growth rate and viability steadily improved. The population doubling time was calculated to be 73.1 hours over approximately 7 weeks; this decreased to 47.4 hours over the subsequent 20 days then stabilised. Antibody secretion remained high at levels in excess of 60 μg/ml. It was determined that the gene copy number in these cells did not decrease according to band intensity using Northern blot analysis.

In fermenters, these cells produced antibody in excess of 70 μg/ml and regularly achieved levels of 100 μg/ml or more. These cells are donated C1H 3D11* 44.

WCM4 Medium

Iscoves DMEM (Iscoves N and Melcher (1978), J. Exp. Med. 1, 47, 923) modified to exclude BSA, transferrin and lecithin.

| | | |
|---|---|---|
| + | 5 ml/litre | 200 mM L glutamine |
| + | 50 mg/litre | L proline |
| + | 50 mg/litre | L threoline |
| + | 50 mg/litre | L methionine |
| + | 50 mg/litre | L cysteine |
| + | 50 mg/litre | L tyrosine |
| + | 25 mg/litre | ascorbic acid |
| + | 0.062 mg/litre | vitamin B6 |
| + | 1.36 mg/litre | vitamin B12 |
| + | 0.2 mg/litre | lipoic acid |
| + | 0.088 mg/litre | methyl linoleate |
| + | 1 µM | methotrexate |
| + | 1 mg/litre | $FeSO_4$ |
| + | 1 mg/litre | $ZnSO_4$ |
| + | 0.0025 mg/litre | $CuSO_4$ |
| + | 5 mg/litre | recombinant insulin (Nucellin) |
| + | 50,000 Iu/litre | polymyxin |
| + | 20,000 Iu/litre | neomycin |
| + | 0.16 mg/litre | putrescine-2 HCL. |

C1H 3D11*44 cells from previous stage which had been growing serum-free for over 2 months were transferred to a SGi 1 liter fermenter with a stainless steel angled paddle turning at 70 rpm. The temperature was set at 37° C., $dO_2$ at 10% and pH control to 7–7.2. The fermenter was seeded on day 0 with $0.22 \times 10^6$ cells/ml in WCM4 medium with 0.1% polyethylene glycol (PEG) 10,000 and 0.25% soy peptone, and was top gassed with $O_2$. The cells were routinely passaged using fresh medium and a split rate typically between 1 to 2 and 1 to 4.

On day 33 the top gassing was replaced with deep sparging which is expected to cause more physical damage to the cells.

On day 50 onwards WCM5 (see Table below) was used together with peptone and PEG instead of WCM4.

On day 53 the PEG was replaced with 0.1% pluronic F68. The resulting growth and antibody levels achieved were in excess of 100 µg/ml in fermenters.

WCM5 Medium

Iscoves DMEM modified to exclude BSA, transferrin and lecithin.

| | | |
|---|---|---|
| + | 5 ml/litre | 200 mM L glutamine |
| + | 50 mg/litre | L proline |
| + | 50 mg/litre | L threonine |
| + | 50 mg/litre | L methionine |
| + | 50 mg/litre | L cysteine |
| + | 50 mg/litre | L tyrosine |
| + | 25 mg/litre | L ascorbic acid |
| + | 0.062 mg/litre | Vitamin B6 |
| + | 1.36 mg/litre | Vitamine B12 |
| + | 2 mg/litre | Ferric citrate |
| + | 1 mg/litre | Zinc sulphate |
| + | 0.0025 mg/lit | Copper sulphate |
| + | 50,000 IU/litre | Polymyxin |
| + | 20,000 IU/litre | Neomycin |
| + | 3 µl/litre | Ethanolamine |
| + | 0.16 mg/litre | Putrescine |
| + | 5 mg/litre | Recombinant Insulin (Nucellin) |

All components in WCM4 and WCM5 are commercially available.

EXAMPLE 3

Purification of Campath 1H (G Dev –95)

Materials and Methods

The purification method used was based on chromatagraphy through three columns. The gels used were 7.85 ml Protein A Sepharose 4 Fast Flow, Pharmacia code No. 17-0974-04 (10 cm×1 cm); 7.85 ml S Sepharose Fast Flow cation exchanger, Pharmacia code No. 17-0511-01 (10 cm×1 cm); and 120 ml Superdex 200 size exclusion medium, Pharmacia code No.17-1046-01 (60 cm×1.6 cm). Each column was protected by a 0.2 µm Gelman Acro sterilising filter.

Preparation of equipment and solutions

The hardware of the protein A column system was washed through with 1N NaOH and left in this solution for 24 hours to remove endotoxin. The gel was then packed into the Pharmacia C10/20 column and sanitized with 2% hibitane gluconate in 20% ethanol. Since, according to the manufacturer, S Sepharose and Superdex 200 gels are both stable in 1N NaOH for prolonged periods these gels were packed into their columns (a Pharmacia C10/20 and a C16/100 column respectively) washed through with 1N NaOH and then left to stand in this solution for 24 hours to remove endotoxin and sanitize the column systems.

The solutions for column operation and sanitization were manufactured using pyrogen free distilled water and sterile filtered to 0.2 µm through Millipore Millipack 100 filters. Samples of all solutions were assayed for endotoxin by LAL test and only those with low values subsequently used.

Column operation

Protein A Sepharose 4 Fast Flow gel.

Tissue culture medium from Example 1 containing Campath 1H antibody was supplied and filtered to 0.2 µm through a sterile PALL posidyne SLK7002 NFZP filter in a Sealkleen housing. The 2% hibitane gluconate in 20% ethanol used to sanitize the protein A column system was removed with distilled water and the system equilibrated with the tris buffered saline pH 7.5 (T.B.S.). The protein A column was then loaded with 1.75 litres of crude Campath 1H (71.4 mg) at a flow rate of 300 cm/hour (235 ml/hour) at a temperature of 20° C.±5° C. Unbound material was washed from the column system with 5 bed volumes (39.25 ml.) of T.B.S. pH 7.5 at the same flow rate. The Protein A gel was eluted at 300 cm/hour with 0.1M citric acid pH 3.0 for <24 hours at room temperature. The elution profile was monitored at A280 nm using a Pharmacia UV1 single path monitor and the protein peak isolated. The elution peak volume was 18.9 ml and 1 ml of this was removed and assayed for Campath 1H by ELISA as described below.

S. Sepharose Fast Flow gel

The 1N NaOH was washed from the S. Sepharose column system with 20 mM Hepes pH 7.5 until the column washings were at pH 7.5. The remaining 17.9 ml. of Protein A column eluate was loaded onto the column at a flow rate of 300 cm/hour (235 ml/hour). Unbound material was washed from the column system with 7 bed volumes (55 ml) of 20 mM Hepes pH 7.5 at the same flow rate. The S. Sepharose gel was eluted by a step elution, using 0.2M NaCl in 20 mM Hepes pH 7.5 at a flow rate of 300 cm/hour. The elution peak was collected by trace using a Pharmacia UV1 monitor at A280 nm (2 mm path length 0.5 AUFS). Eluate collection was started at approximately 20% deflection and continued until the trace had declined to 70% deflection. The elution volume was 10 ml and 1 ml of this was sampled for assay for Campath 1H by ELISA as described below.

Superdex 200 gel

The 1N NaOH was washed from the Superdex column system with PBS pH 7.2 until the column washings were at pH 7.2. The remaining 9 ml of S Sepharose eluate was loaded onto the Superdex column with a syringe via a Millipore Millex GV filter and the filter washed through with 2 ml of PBS pH 7.2. The column was developed with PBS pH 7.2 at 30 cm/hour (60 ml/hour). The size exclusion peaks were monitored using a Pharmacia UV1 monitor at A280 nm. As the peaks eluted fractions were taken in order to separate the aggregate peak from the monomer peak, the monomer peak fraction had a volume of 17.6 ml.

Enzyme Linked Immunosorbent Assay (ELISA)

This is a standard Sandwich Enzyme Immunoassay (Reference) in which anti-human IgG, made from immune-purified goat antiserum, is attached to the solid phase as a capture layer. Detection of captured antigen (Campath 1H Ig) is achieved with a peroxidase—labelled goat anti-human IgG. The assay is sequential with samples of Campath 1H being diluted in a buffer containing casein and hydrolysed gelatin. Incubation periods of 1 hour and 30 minutes, are used at temperature of 37° C. 3',3',5,5'Tetramethylbenzidine (TMB) chromagen plus hydrogen peroxide substrate are added to reveal any bound peroxidase. Optical densities at 450 nm can be determined and Campath 1H concentrations read from a standard curve of known concentrations ranging from 3.9 ng to 250 ng of purified Campath 1H.

Testing of purified Campath 1H

The protein content of the monomer peak was estimated at A280 nm using an extinction coefficient ($E^{1\%}_{1\,cm}$) of 1.35 (optionally 1.32) and a sample examined for aggregate content by HPLC size exclusion column. The remaining material was sterile filtered through a Millipore Millex GV filter (0.2 um pore size) and filled into 29 0.5 ml aliquots in sterile Sarstedt tubes. The majority of the sample tubes were stored at 4° C. however 6 tubes were stored at −70° C. Samples from 4° C. storage were sent for assays as detailed in the following examples.

Results and Discussions

The Campath ELISA results are shown in the table below.

| | Campath 1 H | | | | |
|---|---|---|---|---|---|
| Sample | Titre by ELISA | Vol. (ml) of bulk | Total mg C1 H in bulk | Wgt. C1 H applied next col. | % recovery/ column |
| Crude | 40.8 ug/ml | 1750 | 71.4 | 71.4 | — |
| Protein A eluate | 4.2 mg/ml | 18.9 | 79.4 | 75.2 | 111.2 |
| S sepharose eluate | 6.4 mg/ml | 10.0 | 64.0 | 57.6 | 85.0 |
| Superdex monomer | 2.5 mg/ml | 17.6 | 44.0 | — | 76.4 |

The overall recovery across the three column system, based on the recovery across each column is 61.6%.

| Endotoxin content by LAL test | |
|---|---|
| Sample | Eu/ml |
| Crude | 1.25 |
| Superdex monomer peak | <0.625 |

EXAMPLE 4

Figure 2:
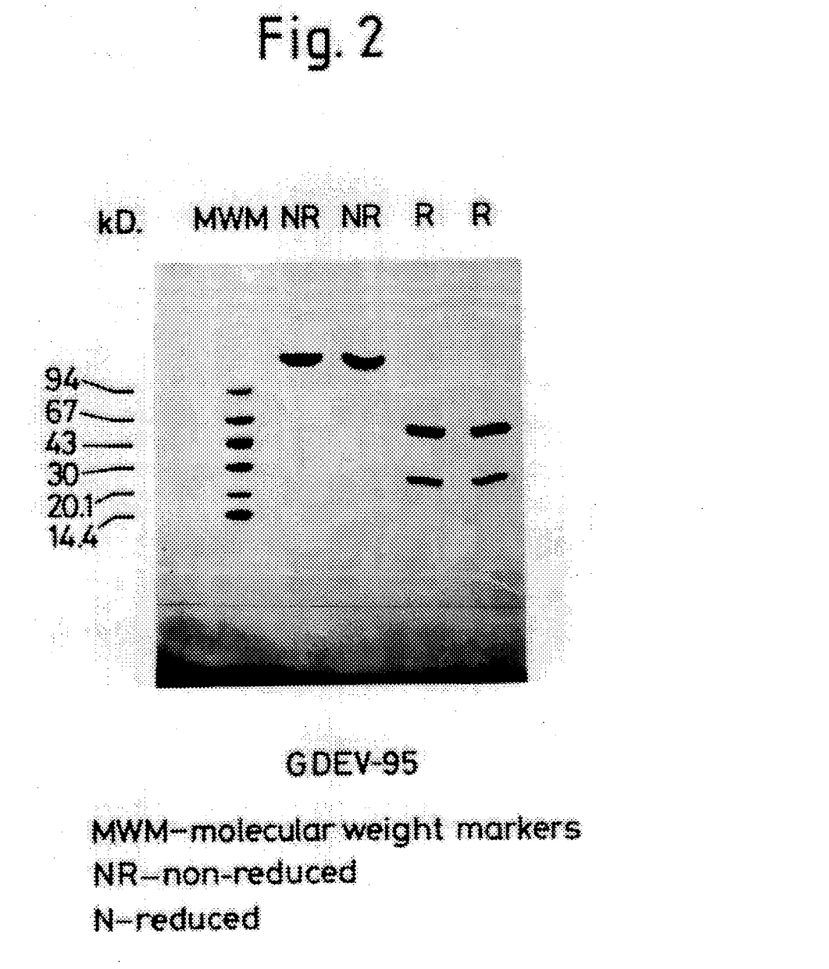

Conventional SDS polyacrylamide gel electrophoresis was carried out on a flat bed 8–18% gradient Pharmacia Excelgel. The results are shown in FIG. 2.

EXAMPLE 5

Characterisation of Campath 1H by reversed phase high performance liquid chromatography.

A 50 μl sample of the product of Example 3 (designated G-Dev −95) in phosphate buffered saline (PBS) at a concentration of 2.4 mg/ml was subjected to reversed phase high performance liquid chromatography (RP-HPLC) under the following conditions:

Column: PLRP-S 1000° A (pore size); 8 μM (particle size) 15×0.46 cm from Polymer Laboratories Ltd UK.

Mobile phase utilised a formic acid/water/acetonitrile system:

Component A—Formic acid: water (5:3).

B—$CH_3CN$.

in the following gradient:

| % A | 80 | 80 | 65 | 0 | 0 | 80 | 80 |
|---|---|---|---|---|---|---|---|
| % B | 20 | 20 | 35 | 100 | 100 | 20 | 20 |
| Time (mins) | 0 | 5 | 38 | 41 | 50 | 51 | 65 |

The column was run at ambient temperature at a flow rate of 1 ml/min$^{-1}$ and UV detection on LDC Spectro Monitor D variable wavelength was carried out at a wavelength of 280 nm with a sensitivity of 0.1 a.u.f.s.

Result

Figure 3:
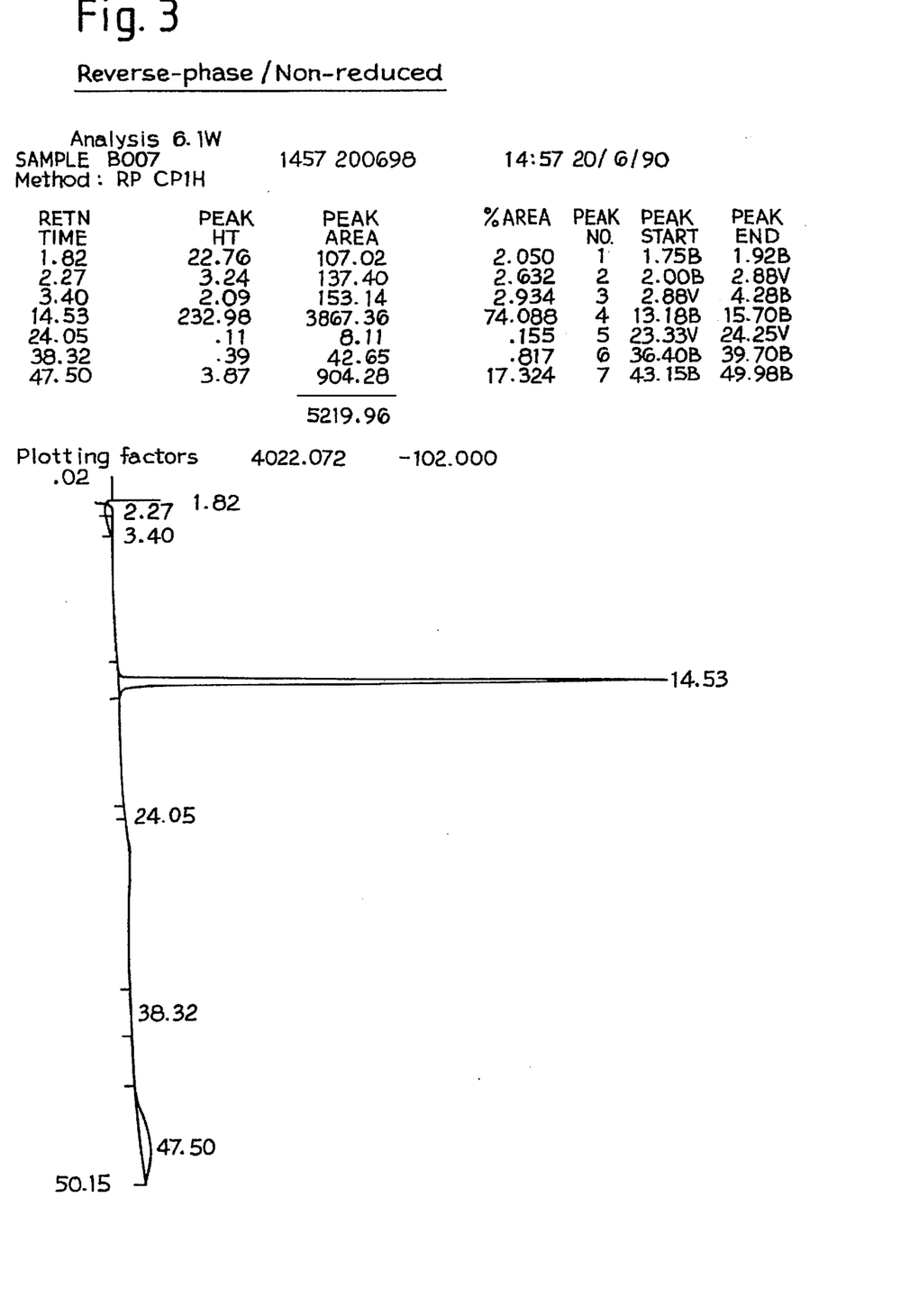

As can be seen in FIG. 3 chromatography of Campath 1H utilising the above system gave a single sharp peak. The peaks eluting after 30 minutes are due to the mobile phase.

EXAMPLE 6

Characterisation of reduced and carboxymethylated Campath 1 by reverse phase high performance liquid chromatography (RPHPLC)

6a. Reduction and carboxymethylation of Campath 1H

Campath 1H may be reduced into its component heavy and light chains by utilising standard reduction and carboxymethylation procedures, which firstly reduce the disulphide bonds and prevents them reforming by alkylating the free thiol groups.

To 1 ml Campath 1H G Dev −95 from Example 3, in phosphate buffered saline at a concentration of 2.4 mg/ml was added 1 ml of 8M Guanidinium chloride in 0.5M Tris/HCl pH 9.0 buffer and 120 μl of 7% Dithiothreitol in the same buffer. The mixture was incubated for two hours at 37° C.

After incubation 120 μl of 9% iodoacetic acid in 0.5M Tris/HCl buffer was added and the mixture was left in the dark for 1 hour. The resulting reduced carboxymethylated material was designated Campath 1H RCM.

6b. RP HPLC characterisation of Campath 1H RCM

30 μl of the material from Example 6a was subjected to reverse phase high performance liquid chromatography under the following conditions.

Column PLRP-S 1000° A (pore size); 8μ(particle size) 15×0.46 cm from Polymer laboratories Ltd UK.

Mobile phase used a water, formic acid and acetonitrile gradient as depicted in the table below:

A—Formic acid
B—Water
C—Acetonitrile

| %       | A | 50 | 50 | 29.4 | 0   | 0   | 50   | 0  |
|---------|---|----|----|------|-----|-----|------|----|
| %       | B | 35 | 35 | 20.6 | 0   | 0   | 35   | 35 |
| %       | C | 15 | 15 | 50   | 100 | 100 | 15   | 15 |
| Time (mins) | | 0 | 5  | 70   | 72  | 82  | 82.1 | 95 |

The column was run at a flow rate of 1 ml/min at ambient temperatures and followed by UV absorbance at a wavelength of 280 nm a.u.f.s.

Result

Figure 4:
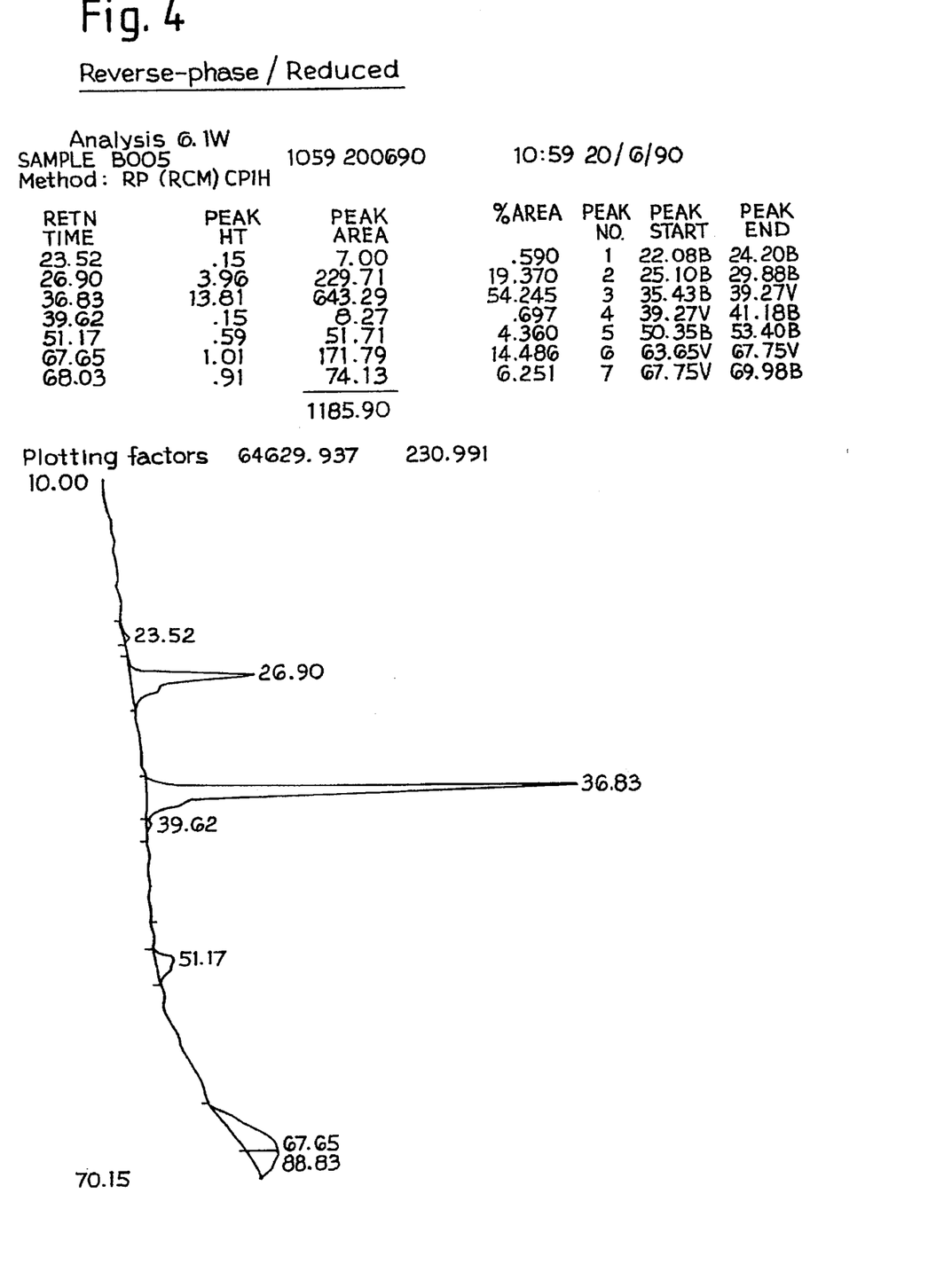

As can be seen from FIG. 4, the resulting material resolves into two peaks, corresponding to the heavy and light chains.

EXAMPLE 7

Characterisation of Campath 1H by high performance size exclusion chromatography for the determination of high molecular weight components in Campath 1H.

A 50 μl sample of the product of Example 3 (G-Dev −95) in phosphate buffered saline (at a concentration of 2.4 mg/ml) was subjected to high performance size exclusion chromatography under the following conditions.

Column—TSK gel G3000 SW×1 30 cm×0.78 cm i.d.

Mobile phase—0.05M $Na_2HPO_4$+0.1M $Na_2SO_4$ adjusted with $H_3PO_4$ to pH 6.8

Flow rate—0.75 ml/min$^{-1}$

The column was run for twenty four minutes at ambient temperature and followed by UV absorbance at a wavelength of 280 nm.

A second 50 μl sample using Campath 1H reduced in accordance with Example 6a) was analysed by the same method.

Figure 5:
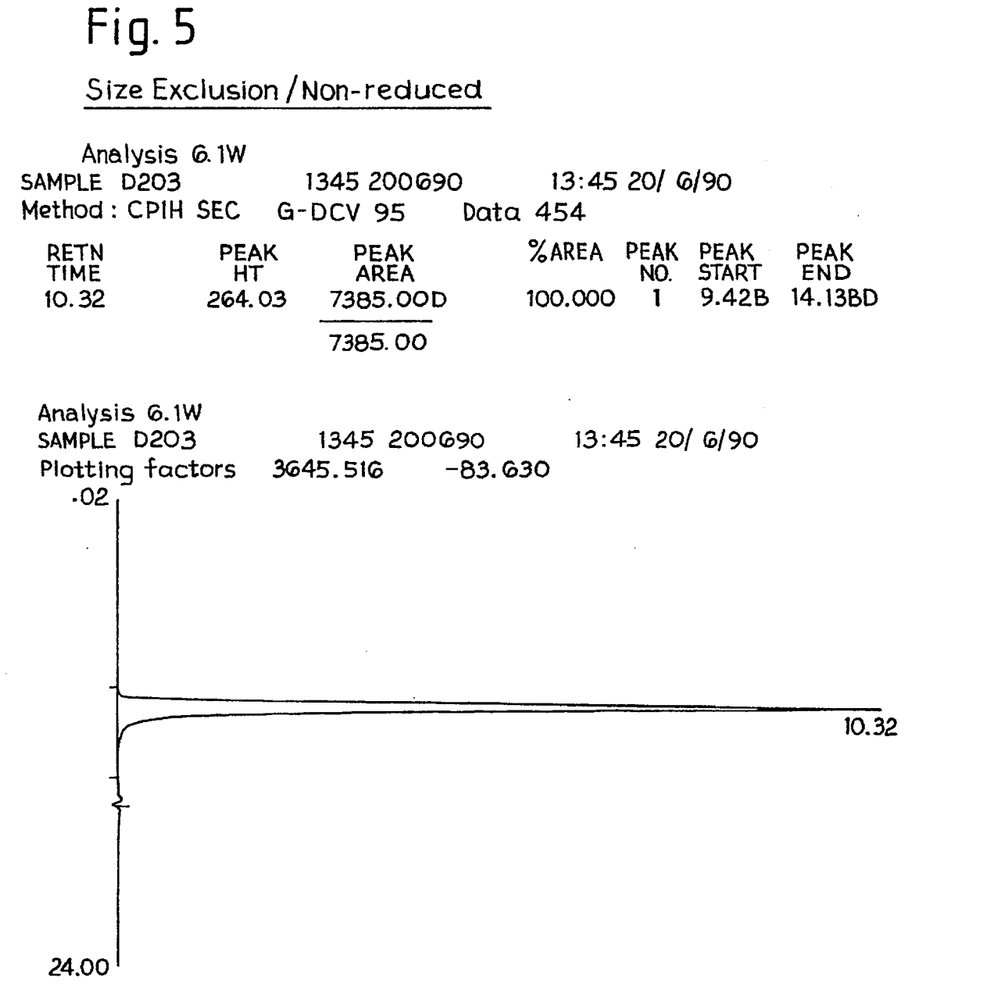
Figure 6:
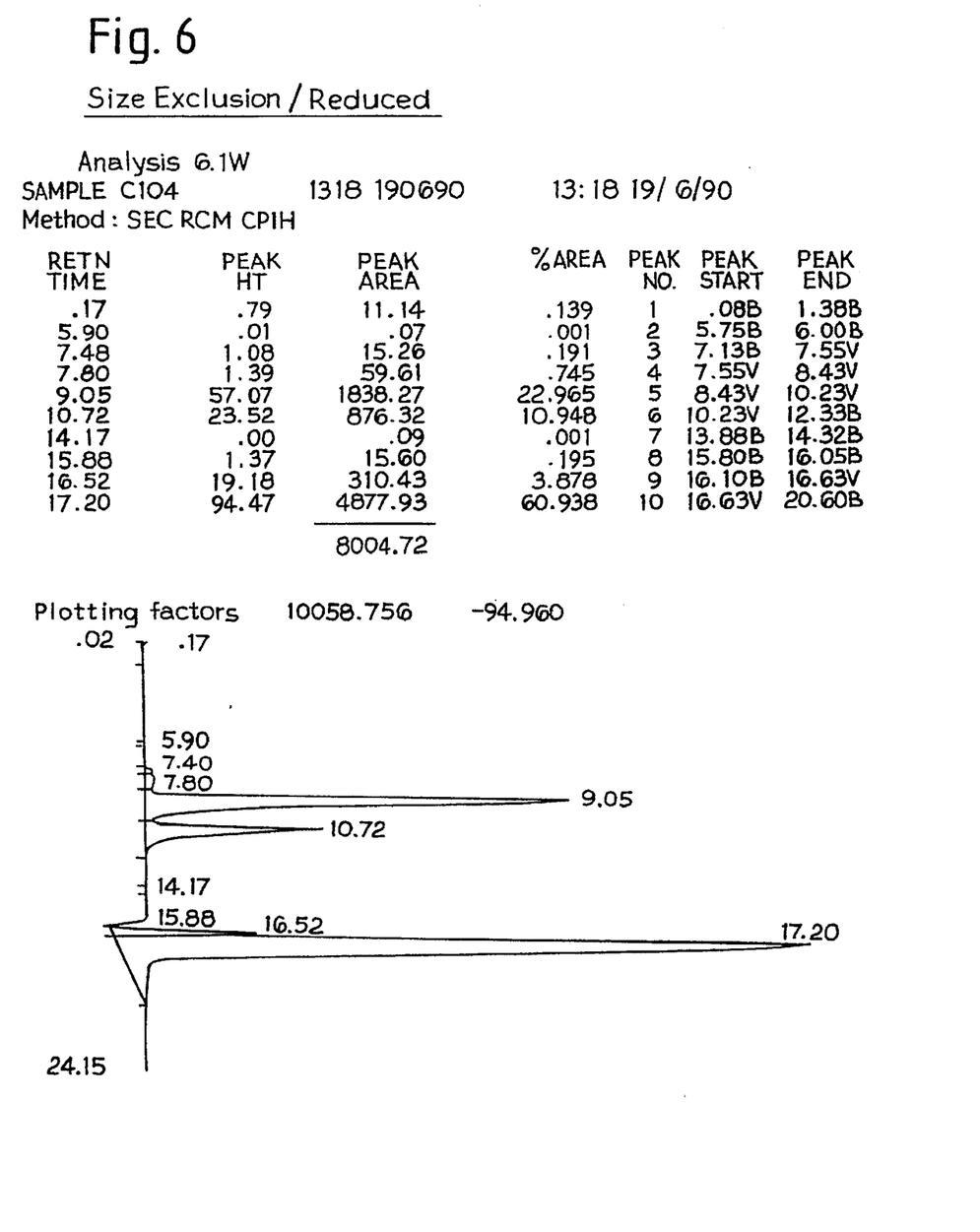

Results:

The results in FIG. 5 show a clean single peak indicating low levels of aggregate. Levels of between 0.5 and 2.0% are generally achieved. The results in FIG. 6 show two main peaks corresponding to heavy and light chains in expected ratio. The peaks at total permeation volumn (ca.15–18 minutes) are due to reagents.

Biological assays for functional purified Campath 1H

Complement lysis assay for Campath 1H

The complement lysis assay is a measure of antibody function expressed as specific activity, determined by the ability of a purified preparation of an anti-CDW52 antibody of known concentration to bind to a pre-determined number of cells and effect cell lysis.

The assay is carried out on Campath 1H using Karpas 422 cells (established from B-cell non-Hodgkin lymphoma cell line—Dyer et al (1990) Blood, 75 704–714) expressing Campath antigen on the cell surface. $1.2 \times 10^7$ cells were loaded with radiolabel by incubating for 2 hours at 37° C. in a $CO_2$ incubator in the presence of 600 μCi of $^{51}Cr$ (sodium chromate).

5.3 ml of the loaded cells in medium (total volume 23.5 ml), were added to 12.5 ml of normal human serum and 150 μl of the mixture were pipetted into the wells of a microtitre plate.

50 μl samples of the final eluate from three purification runs were mixed with the cells and incubated for 30 minutes at 4° C. followed by 90 minutes at 37° C. The culture was centrifuged at 2000 rpm for 5 minutes and the radioactivity in 100 μl of cell supernatant was counted on a gamma counter. Complement lysis activity in Kilo Units/ml was calculated from a standard curve of a reference preparation (1000 Units/ml).

The results are set out in Table 3.

The concentration of Campath 1H in the 50 μl samples of final eluate was estimated using samples in PBS pH 7.2 read on a spectrophotometer at 280 nm. The results are expressed in Table 3 as optical density in mg/ml.

From this data the specific activity in Kilo Units/mg is determined by using the equation: KU/ml/

TABLE 3

| Sample | Complement lysis Kilo Units/ml | Protein Conc mg/ml | Specific Activity in Kilo Units |
|--------|-------------------------------|--------------------|---------------------------------|
| A      | 11.2                          | 11.1               | 1.0                             |
| B      | 14.8                          | 14.2               | 1.0                             |
| C      | 13.7                          | 13.6               | 1.0                             |

The results indicate that purified preparations of Campath 1H are functional

We claim:

1. A process for obtaining a purified IgG antibody preparation which comprises:

(a) culturing a recombinant mammalian cell line capable of producing the antibody in an aqueous culture medium under antibody producing conditions;

(b) applying the antibody-containing aqueous medium to a Protein A column or Protein G column so as to absorb the antibody onto the column and then eluting the antibody with an acidic solution to produce an acidic eluate;

(c) applying the acidic eluate to an ion exchange column of charged particles previously equilibrated with a neutral buffer so as to absorb the antibody and then eluting the antibody with a neutral aqueous solution of counter-charged ions; and (d) applying the aqueous eluate to a size exclusion column of porous particles so as to separate aggregates and other non-antibody molecules from the desired antibody and to obtain the desired antibody in selected fractions eluted from the column.

2. A method in accordance with claim 1, wherein the antibody-containing aqueous medium is filtered by an ultrafiltration step before being applied to the Protein A or Protein G column.

3. A method in accordance with claim 1, wherein the antibody-containing aqueous medium is applied to a Protein A column.

4. A method in accordance with claim 3, wherein the Protein A column is a Protein A sepharose column.

5. A method in accordance with claim 3, wherein the column is eluted with citric acid.

6. A method in accordance with claim 1, wherein the ion exchange column is a cation exchange column.

* * * * *